(12) United States Patent
Grothe et al.

(10) Patent No.: US 10,413,318 B2
(45) Date of Patent: Sep. 17, 2019

(54) ROTATIONAL SYSTEMS COMPRISING A POLYMER DRIVESHAFT

(71) Applicant: Cardiovascular Systems, Inc., New Brighton, MN (US)

(72) Inventors: Preston L. Grothe, Maple Grove, MN (US); Matthew D. Cambronne, North Oaks, MN (US); Joseph P. Higgins, Minnetonka, MN (US); William F. Kuester, III, Goodyear, AZ (US); Benjamin Haselman, St. Paul, MN (US); Joshua J. Cranston, Andover, MN (US); Ric A. Gould, Brooklyn Park, MN (US); Nicholas W. Rydberg, Oakdale, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 413 days.

(21) Appl. No.: 15/168,881

(22) Filed: May 31, 2016

(65) Prior Publication Data

US 2016/0346003 A1    Dec. 1, 2016

Related U.S. Application Data

(60) Provisional application No. 62/169,002, filed on Jun. 1, 2015, provisional application No. 62/184,399, filed
(Continued)

(51) Int. Cl.
*A61B 17/3207* (2006.01)
*A61B 17/32* (2006.01)
(Continued)

(52) U.S. Cl.
CPC ........ *A61B 17/320758* (2013.01); *A61B 2017/0084* (2013.01); *A61B 2017/320004* (2013.01);
(Continued)

(58) Field of Classification Search
CPC ........ A61B 17/320758; A61B 2017/320766; A61B 2017/320004; A61B 2017/0084;
(Continued)

(56) References Cited

U.S. PATENT DOCUMENTS 5,669,920 A     9/1997  Conley et al.
5,879,282 A *   3/1999  Fischell ............... A61N 5/1002
                                                    600/3
(Continued)

FOREIGN PATENT DOCUMENTS

EP          1875871          9/2008

OTHER PUBLICATIONS

International Preliminary Report on Patentability dated Dec. 5, 2017 for PCT Application No. PCT/US2016/035129, filed Jun. 1, 2016.
(Continued)

*Primary Examiner* — Phong Son H Dang
(74) *Attorney, Agent, or Firm* — Barnes & Thornburg LLP; Jeffrey R. Stone (57) ABSTRACT

Various embodiments of devices and systems comprising a polymer driveshaft for use in high-speed rotational medical procedures, e.g., atherectomy, are disclosed. Generally, the primary driveshaft for transferring torque and activating rotation of a tool attached thereto, e.g., an abrasive element, is constructed with at least a polymer outer and inner surface. In certain embodiments, the polymer driveshaft may comprise a metallic band for fixed attachment of a structure, e.g., an abrasive element, thereto. Various embodiments may comprise a coupler that connects a drive shaft connected with a prime mover, e.g., a turbine or electric motor, with the polymer drive shaft, the coupler comprising openings through the coupler wall to the inner diameter of the coupler to allow fluid flow to the inner diameter of the coupled polymer drive shaft.

21 Claims, 6 Drawing Sheets

Related U.S. Application Data on Jun. 25, 2015, provisional application No. 62/279,379, filed on Jan. 15, 2016, provisional application No. 62/184,358, filed on Jun. 25, 2015.

(51) Int. Cl.
  *A61B 17/00* (2006.01)
  *A61B 90/00* (2016.01)

(52) U.S. Cl.
  CPC ............ *A61B 2017/320032* (2013.01); *A61B 2017/320766* (2013.01); *A61B 2090/3966* (2016.02); *A61B 2217/007* (2013.01)

(58) Field of Classification Search
  CPC ...... A61B 2017/320032; A61B 17/007; A61B 2090/3966
  See application file for complete search history.

(56) References Cited

U.S. PATENT DOCUMENTS

| | | | | |
|---|---|---|---|---|
| 5,897,566 A * | 4/1999 | Shturman | ...... | A61B 17/320758 606/159 |
| 5,941,869 A * | 8/1999 | Patterson | ........... | A61B 17/3207 604/22 |
| 6,027,460 A * | 2/2000 | Shturman | ......... | A61M 25/0133 600/129 |
| 6,132,444 A * | 10/2000 | Shturman | ...... | A61B 17/320758 128/858 |
| 6,494,890 B1 * | 12/2002 | Shturman | ...... | A61B 17/320758 606/159 |
| 2003/0028173 A1 | 2/2003 | Forsberg | | |
| 2005/0137519 A1 * | 6/2005 | Boismier | ................ | A61L 29/02 604/19 |
| 2005/0149083 A1 * | 7/2005 | Prudnikov | ..... | A61B 17/320758 606/159 |
| 2006/0106361 A1 * | 5/2006 | Muni | .................... | A61B 5/411 604/500 |
| 2007/0093781 A1 * | 4/2007 | Kugler | ................. | A61B 17/221 604/510 |
| 2007/0225750 A1 * | 9/2007 | Ren | ......................... | A61F 2/013 606/200 |
| 2009/0024085 A1 * | 1/2009 | To | .................. | A61B 17/320758 604/95.01 |
| 2009/0041923 A1 * | 2/2009 | Lin | ...................... | A61L 29/085 427/2.3 |
| 2009/0069829 A1 | 3/2009 | Shturman | | |
| 2010/0004631 A1 * | 1/2010 | Zhou | .................... | A61L 29/085 604/527 |
| 2010/0121361 A1 * | 5/2010 | Plowe | ............ | A61B 17/320758 606/159 |
| 2010/0249602 A1 * | 9/2010 | Buckley | .................... | A61B 8/12 600/467 |
| 2012/0077049 A1 * | 3/2012 | Lin | ........................ | A61L 27/34 428/520 |
| 2012/0101480 A1 * | 4/2012 | Ingle | ................. | A61M 25/0009 604/526 |
| 2012/0109170 A1 * | 5/2012 | Shturman | ...... | A61B 17/320758 606/159 |
| 2012/0109171 A1 | 5/2012 | Zeroni et al. | | |
| 2012/0253186 A1 * | 10/2012 | Simpson | ........ | A61B 17/320758 600/426 |
| 2014/0107681 A1 | 4/2014 | Davies et al. | | |
| 2015/0258258 A1 * | 9/2015 | Bonnette | ............. | A61M 1/0084 606/159 |
| 2016/0051323 A1 * | 2/2016 | Stigall | ...................... | A61B 8/12 600/407 |
| 2017/0066227 A1 * | 3/2017 | Brusi | ..................... | B32B 27/08 |

OTHER PUBLICATIONS

Supplementary European Search Report issued in EP 16804269.5, dated Jan. 8, 2019.

\* cited by examiner

ROTATIONAL SYSTEMS COMPRISING A POLYMER DRIVESHAFT

CROSS-REFERENCE TO RELATED APPLICATIONS

This application claims the benefit of U.S. Provisional Application No. 62/169,002, filed Jun. 1, 2015 and entitled POLYMER DRIVESHAFT FOR HIGH-SPEED ROTATIONAL MEDICAL PROCEDURES; U.S. Provisional Application No. 62/184,399, filed Jun. 25, 2015 and entitled DEVICES, SYSTEMS AND METHODS FOR PERFORMING ATHERECTOMY PROCEDURES WITH POLYMER DRIVE SHAFT WITH METALLIC MARKER BAND; U.S. Provisional Application No. 62/184,358, filed Jun. 25, 2015 and entitled DEVICES, SYSTEMS AND METHODS FOR PERFORMING ATHERECTOMY PROCEDURES WITH POLYMER OR NON-POLYMER DRIVE SHAFTS COMPRISING A DRIVE SHAFT COUPLER; and U.S. Provisional Application No. 62/279,379, filed Jan. 15, 2016 and entitled POLYMER DRIVESHAFT FOR USE IN ORBITAL AND ROTATIONAL ATHERECTOMY, the entirety of each of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The disclosure relates to devices and methods using guidewires, for example intravascular procedures, e.g., removing tissue from body passageways, such as removal of atherosclerotic plaque from arteries with, e.g., a rotational atherectomy device. More specifically, the disclosure provides a guidewire tip that is reformable and, therefore, resistant to damaging deformation.

Description of the Related Art

A variety of techniques and instruments have been developed for use in the removal or repair of tissue in arteries and similar body passageways. A frequent objective of such techniques and instruments is the removal of atherosclerotic plaques in a patient's arteries. Atherosclerosis is characterized by the buildup of fatty deposits (atheromas) in the intimal layer (under the endothelium) of a patient's blood vessels. Very often over time, what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Rotational atherectomy procedures have become a common technique for removing such stenotic material. Such procedures are used most frequently to initiate the opening of calcified lesions in coronary arteries. Most often the rotational atherectomy procedure is not used alone, but is followed by a balloon angioplasty procedure, which, in turn, is very frequently followed by placement of a stent to assist in maintaining patency of the opened artery. For non-calcified lesions, balloon angioplasty most often is used alone to open the artery, and stents often are placed to maintain patency of the opened artery. Studies have shown, however, that a significant percentage of patients who have undergone balloon angioplasty and had a stent placed in an artery experience stent restenosis, which is blockage of the stent that most frequently develops over a period of time as a result of excessive growth of scar tissue within the stent. In such situations an atherectomy procedure is the preferred procedure to remove the excessive scar tissue from the stent (balloon angioplasty being not very effective within the stent), thereby restoring the patency of the artery.

Several kinds of rotational atherectomy devices have been developed for attempting to remove stenotic material. In one type of device, such as that shown in U.S. Pat. No. 4,990,134 (Auth), a burr covered with an abrasive abrading material such as diamond particles is carried at the distal end of a flexible drive shaft. The burr is rotated at high speeds (typically, e.g., in the range of about 150,000-190,000 rpm) while it is advanced across the stenosis. As the burr is removing stenotic tissue, however, it blocks blood flow. Once the burr has been advanced across the stenosis, the artery will have been opened to a diameter equal to or only slightly larger than the maximum outer diameter of the burr. Frequently more than one size burr must be utilized to open an artery to the desired diameter.

U.S. Pat. No. 5,314,438 (Shturman) discloses another atherectomy device having a drive shaft with a section of the drive shaft having an enlarged diameter, at least a segment of this enlarged surface being covered with an abrasive material to define an abrasive segment of the drive shaft. When rotated at high speeds, the abrasive segment is capable of removing stenotic tissue from an artery. Though this atherectomy device possesses certain advantages over the Auth device due to its flexibility, it also is capable only of opening an artery to a diameter about equal to the diameter of the enlarged abrading surface of the drive shaft since the device is not eccentric in nature.

U.S. Pat. No. 6,494,890 (Shturman) discloses a known atherectomy device having a drive shaft with an enlarged eccentric section, wherein at least a segment of this enlarged section is covered with an abrasive material. When rotated at high speeds, the abrasive segment is capable of removing stenotic tissue from an artery. The device is capable of opening an artery to a diameter that is larger than the resting diameter of the enlarged eccentric section due, in part, to the orbital rotational motion during high speed operation. Since the enlarged eccentric section comprises drive shaft wires that are not bound together, the enlarged eccentric section of the drive shaft may flex during placement within the stenosis or during high speed operation. This flexion allows for a larger diameter opening during high speed operation, but may also provide less control than desired over the diameter of the artery actually abraded. In addition, some stenotic tissue may block the passageway so completely that the Shturman device cannot be placed therethrough. Since Shturman requires that the enlarged eccentric section of the drive shaft be placed within the stenotic tissue to achieve abrasion, it will be less effective in cases where the enlarged eccentric section is prevented from moving into the stenosis. The disclosure of U.S. Pat. No. 6,494,890 is hereby incorporated by reference in its entirety.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 6,295,712, "ROTATIONAL ATHERECTOMY DEVICE";

U.S. Pat. No. 6,494,890, "ECCENTRIC ROTATIONAL ATHERECTOMY DEVICE";

U.S. Pat. No. 6,132,444, "ECCENTRIC DRIVE SHAFT FOR ATHERECTOMY DEVICE AND METHOD FOR MANUFACTURE";

U.S. Pat. No. 6,638,288, "ECCENTRIC DRIVE SHAFT FOR ATHERECTOMY DEVICE AND METHOD FOR MANUFACTURE";

U.S. Pat. No. 5,314,438, "ABRASIVE DRIVE SHAFT DEVICE FOR ROTATIONAL ATHERECTOMY";

U.S. Pat. No. 6,217,595, "ROTATIONAL ATHERECTOMY DEVICE";

U.S. Pat. No. 5,554,163, "ATHERECTOMY DEVICE";

U.S. Pat. No. 7,507,245, "ROTATIONAL ANGIOPLASTY DEVICE WITH ABRASIVE CROWN";

U.S. Pat. No. 6,129,734, "ROTATIONAL ATHERECTOMY DEVICE WITH RADIALLY EXPANDABLE PRIME MOVER COUPLING";

U.S. patent application Ser. No. 11/761,128, "ECCENTRIC ABRADING HEAD FOR HIGH-SPEED ROTATIONAL ATHERECTOMY DEVICES";

U.S. patent application Ser. No. 11/767,725, "SYSTEM, APPARATUS AND METHOD FOR OPENING AN OCCLUDED LESION";

U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE";

U.S. patent application Ser. No. 12/388,703, "ROTATIONAL ATHERECTOMY SEGMENTED ABRADING HEAD AND METHOD TO IMPROVE ABRADING EFFICIENCY"; and U.S. patent application Ser. No. 13/624,313, "ROTATIONAL ATHERECTOMY DEVICE WITH ELECTRIC MOTOR".

BRIEF SUMMARY OF THE INVENTION

Various embodiments of devices and systems comprising a polymer driveshaft for use in high-speed rotational medical procedures, e.g., atherectomy, are disclosed. Generally, the primary driveshaft for transferring torque and activating rotation of a tool attached thereto, e.g., an abrasive element, is constructed with at least a polymer outer and inner surface. In certain embodiments, the polymer driveshaft may comprise a metallic band for fixed attachment of a structure, e.g., an abrasive element, thereto. Various embodiments may comprise a coupler that connects a drive shaft connected with a prime mover, e.g., a turbine or electric motor, with the polymer drive shaft, the coupler comprising openings through the coupler wall to the inner diameter of the coupler to allow fluid flow to the inner diameter of the coupled polymer drive shaft.

The figures and the detailed description which follow more particularly exemplify these and other embodiments of the invention.

DETAILED DESCRIPTION OF THE INVENTION

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Figure 1:
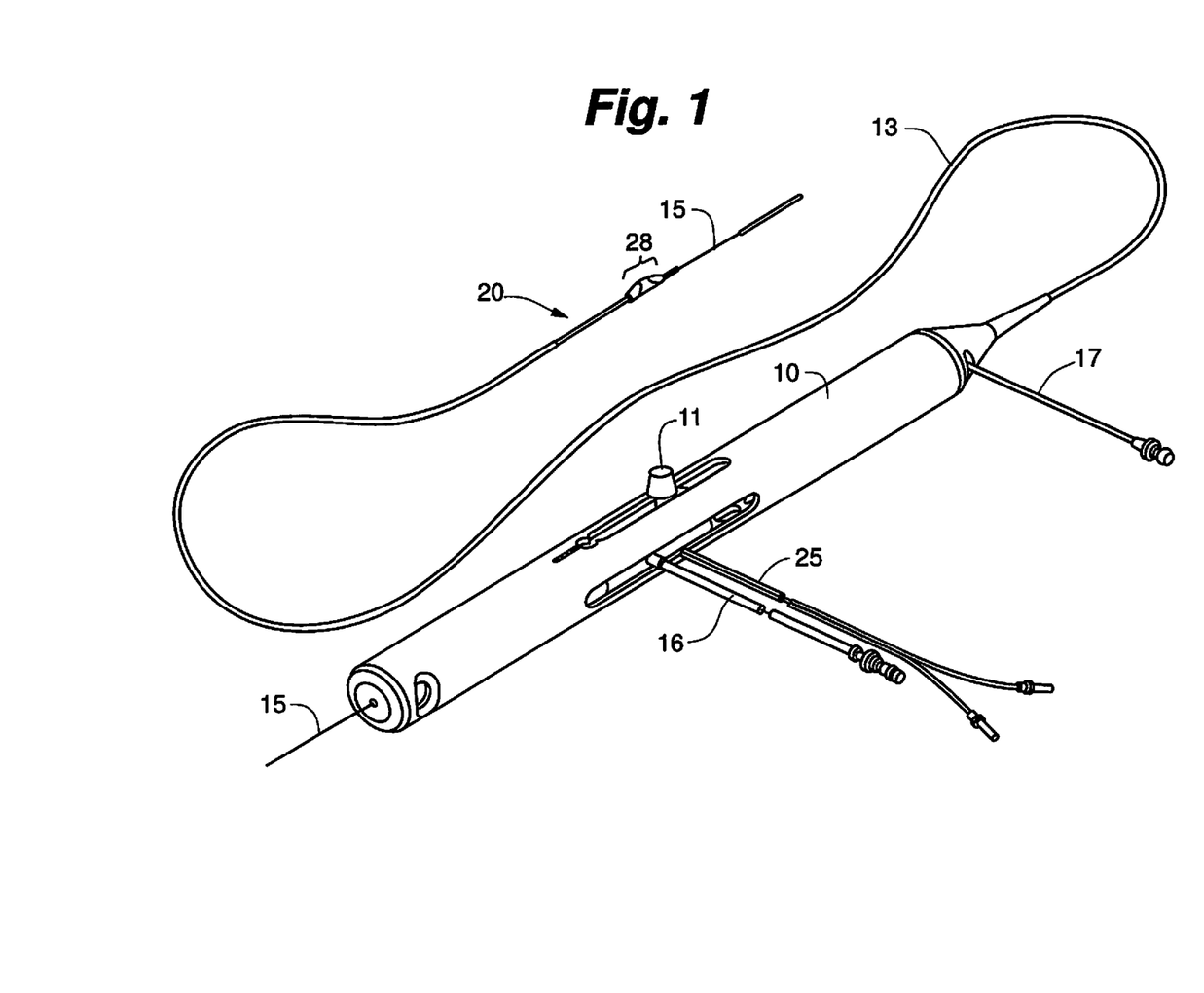
FIG. 1 is a perspective view of one embodiment of a known rotational atherectomy device and system.

FIG. 1 illustrates one known embodiment of a rotational atherectomy device. The device includes a handle portion 10, an elongated, flexible drive shaft 20 having an eccentric enlarged abrading head 28, and an elongated catheter 13 extending distally from the handle portion 10. The drive shaft 20 is constructed from helically coiled wire as is known in the art and an abrasive element 28 is fixedly attached thereto. Known drive shafts are manufactured from a multi-filar wound coil. The inherent construction of this known coil allows for spaces between the filars. These spaces allow fluid, e.g., saline and/or water or other fluid, to pass through to the inner diameter of the drive shaft coil in order to provide cooling and/or lubrication effects to the interface of the drive shaft coil and the guide wire 15.

Generally, in this known construction, a coupler (typically comprising a solid metallic tube) is attached to the proximal end of the coiled drive shaft and to the drive shaft of the handle portion 10, wherein the drive shaft of the handle portion 10 is driven by a prime mover, thereby providing a connection between the prime mover, e.g., a turbine or electric motor, and the drive shaft 20.

Continuing with reference to FIG. 1, the catheter 13 has a lumen in which most of the length of the drive shaft 20 is disposed, except for the enlarged abrading head 28 and a short section distal to the abrasive element 28. The drive shaft 20 also contains an inner lumen, permitting the drive shaft 20 to be advanced and rotated over the guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 25, alternatively a single fiber optic cable may be used, may also be provided for monitoring the speed of rotation of the turbine and drive shaft 20. The handle 10 also desirably includes a control knob 11 for advancing and retracting the turbine and drive shaft 20 with respect to the catheter 13 and the body of the handle.

Figure 2:
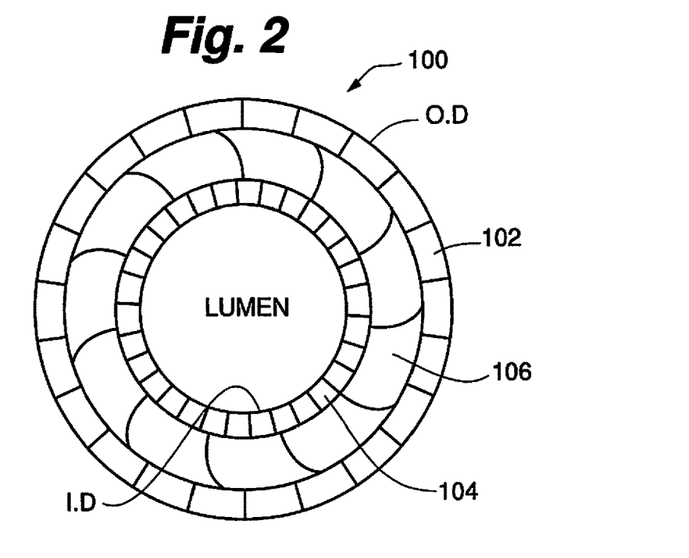
FIG. 2 is a cross-sectional view of one embodiment of the present invention.

Turning now to FIG. 2, an embodiment of a layered polymer driveshaft 100 is illustrated. In this embodiment, the outer layer 102 may comprise nylon, PEEK, polyimide or any composite comprising two or more of these materials. The inner layer 104 may comprise PTFE, polyimide, nylon, PEEK, or any composite comprising two or more of these materials and defines a lumen. The middle layer 106 comprises a flat or round wire coil or braid, a structure that is well known to the skilled artisan.

Figure 3A:
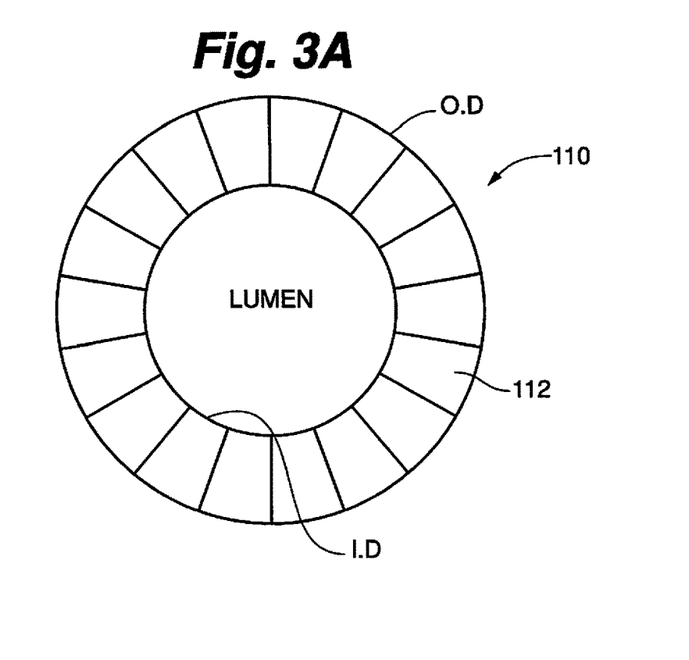
FIG. 3A is a cross-sectional view of one embodiment of the present invention.

FIG. 3A illustrates an end view wherein an alternate embodiment of a polymer driveshaft 110 is comprised entirely of non-metallic elements, i.e., without a middle layer comprising flat wire coil or braid. In this embodiment, the driveshaft may be constructed of a single polymer material layer 112 such as nylon, PEEK, polyimide or any composite of nylon, PEEK and/or polyimide, as illustrated, with lumen defined thereby.

Figure 3B:
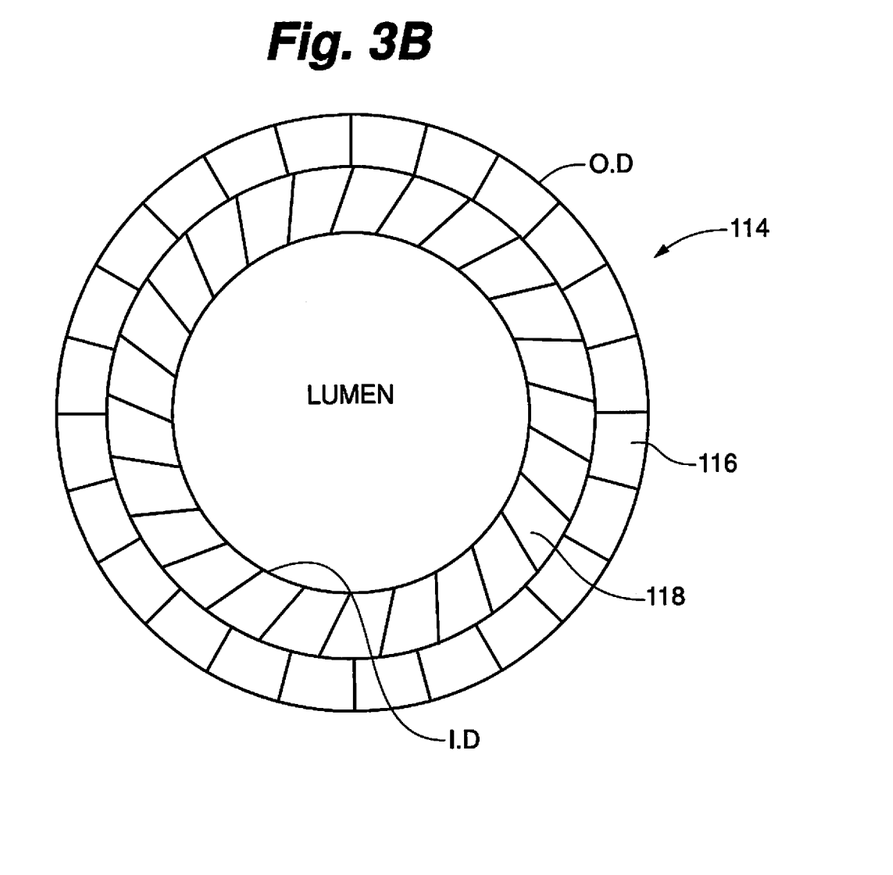
FIG. 3B is a cross-sectional view of one embodiment of the present invention.

Another alternative embodiment of a polymer driveshaft 114 as shown in FIG. 3B, an outer layer 116 may comprise either polyimide (natural or colored) or a nylon, e.g., nylon TR55LX, and an inner layer 118 may comprise PTFE, polyimide or a composite comprising PTFE and polyimide and defining a lumen. This embodiment may be manufactured as a polymer tube that is extruded or dip coated as will be well understood by the skilled artisan.

As discussed above, the driveshaft disclosed herein will comprise at least one tool, typically near the distal end of the driveshaft such as an abrasive element 28 as show in FIG. 1. An exemplary tool comprises an atherectomy tool such as a burr or abrasive crown and may be concentric or eccentric. Other tools may comprise sensors, transceivers, receivers and the like for, inter alia, obtaining, sending and/or receiving data regarding the biological lumen such as position/distance, elastance, compliance, composition, etc., that the polymer driveshaft is received within and/or the region of interest, e.g., a lesion, within the lumen.

The various embodiments comprising a polymer driveshaft as disclosed herein provides particular advantages over the known metal coil filar driveshaft.

1. The known driveshaft 20 augurs fluid when rotating as the inner and outer diameters of the driveshaft 20 is coiled metal. All of the polymer driveshaft embodiments comprise smooth polymer-coated inner and outer diameters and will, therefore, not auger fluid. The benefit of this difference is that the saline flow from the distal end of a rotating device will not change, or change minimally, when the driveshaft is rotating as compared with when the drive shaft is not rotating.

2. The known metal coil drive shaft 20 will eventually weld to the guidewire 15 when rotated without lubrication, a condition that is known to occur on occasion. In contrast, the inner diameter of the disclosed polymer driveshaft embodiments comprises a low friction polymer, e.g., PTFE, that will not weld or otherwise stick to the guide wire 15 when no lubrication is present.

3. Particulate or tissue may flow the inner diameter of the known driveshaft 20 and/or auger along the inner or outer diameter of the wire coiled driveshaft 20 and may result in sticking between the driveshaft 20 and the guidewire 15. In contrast, the presently disclosed polymer driveshaft embodiments may comprise a smooth and continuous outer and inner surface that is impermeable to biological material such as plaque particulate or tissue. And, as discussed above, since the inner and outer diameters are both smooth and continuous polymer structures, no fluid augering or tissue or particulate auguring will occur. The polymer driveshaft embodiments of the present disclosure, therefore, provide a structure that makes it much less likely for any plaque particulate and/or tissue to flow to the driveshaft's inner diameter and, in turn, much less likely for the polymer driveshaft to stick to the guide wire.

4. The known metal coiled driveshaft 20 comprises a wall thickness of 0.006 inches or greater. In contrast, the polymer driveshaft embodiments of the present invention may comprise a wall thickness that is less than 0.006 inches. For example, single material polymer construction may have a wall thickness as small as 0.001 inches, while 3-layer constructions comprising an outer polymer layer, middle metal coil or braid layer and inner polymer layer may comprise wall thickness as small as 0.003 inches. The primary benefit to the smaller wall thickness of the polymer driveshaft embodiments disclosed herein is that the driveshaft itself comprises a smaller or lower profile, with a smaller outer diameter than the known coiled metal driveshaft 20 while still using the standard 0.004 inch core guidewire 15.

5. The known metal coiled driveshaft 20 comprises coiled wires that store axial tension and/or compression that, when released, may spring forward as a spring unexpectedly and result in unwanted trauma to the vessel. In contrast, the polymer driveshaft embodiments disclosed herein will either not store any axial tension or compression in the case of the single material polymer construction embodiment. In addition, the 3-layer polymer construction, comprising a middle metal coil or braid layer 106 sandwiched between inner and outer polymer layers 104, 102, will store much less axial compression than the known all metal coiled driveshafts 20 and, therefore, much less likely to spring forward and with less force than the known driveshaft 20.

6. The known metal coiled driveshaft 20 spins on bare metal guidewires, resulting in wearing of the guidewire coating and, eventually, heat buildup and possible sticking of the driveshaft 20 to the guidewire 15. The polymer inner layer of the present invention comprises a low friction material, e.g., PTFE, that will not wear on guidewire coatings.

7. The known metal coiled driveshaft 20 comprises individual filars that are known to catch the guidewire 15 when advancing through the driveshaft lumen. The polymer driveshaft embodiments of the present invention comprise a smooth and continuous inner diameter that cannot catch the guidewire 15 during advancement therethrough. As a result, the guidewire 15 is easier to load through the inner diameter of the inventive driveshaft embodiments and may be easier to remove the inventive driveshaft off the guidewire 15 after completion of the procedure and thereby enabling easier retention of the guidewire's position in the vessel.

Figure 4:
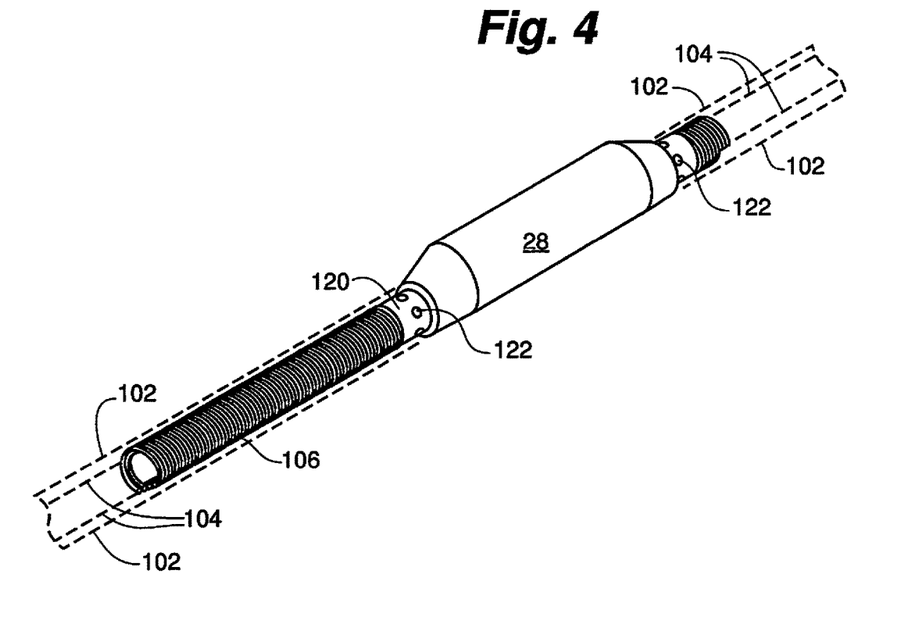
FIG. 4 is a perspective partial cutaway view of one embodiment of the present invention.
Figure 5:
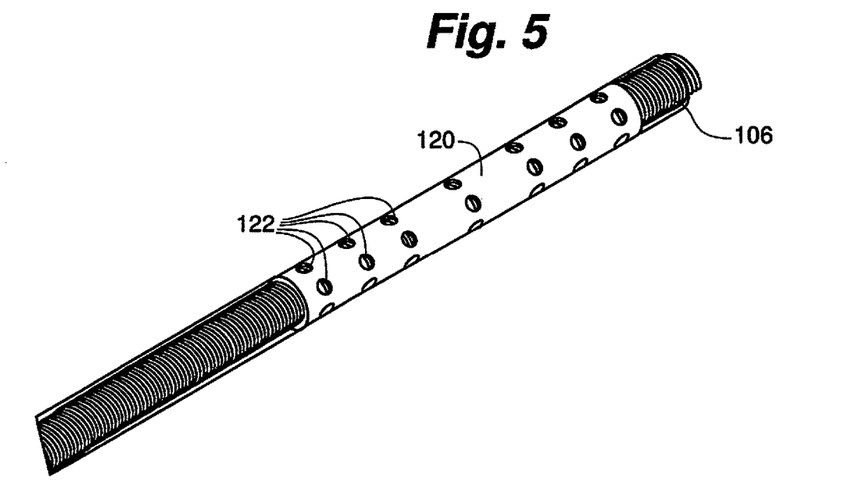
FIG. 5 is a perspective partial cutaway view of one embodiment of the present invention.

Turning now to FIGS. 4 and 5, with continued reference to FIGS. 1-3, an orbital atherectomy drive shaft comprising at least inner and outer polymer layers is provided. An intermediate layer 106 may be provided between the inner and outer polymer layers 104,102 as illustrated. This intermediate layer may comprise a metallic layer 106, e.g., a metallic braid or a metallic coil, positioned between the inner and outer polymer layers 104,102 as described in connection with FIG. 2. As shown in FIGS. 4 and 5, a marker band 120 is attached to the metallic layer 106. In one embodiment, the marker band 120 is affixed to the metallic layer 106 by means known to the skilled artisan including, e.g., welding, adhesive, molding and crimping. In another embodiment, the driveshaft comprises only polymer as in FIG. 3A (single polymer material) or as in FIG. 3B (two polymer materials) and the marker band 120 is embedded within the polymer by heating the polymer and allowing the marker band 120 to sink within the polymer.

As illustrated, the marker band 120 may comprise perforations 122. These perforations 122 may allow additional torsional strength between the inventive polymer driveshaft and the structure, e.g., abrasive element 28, attached to the marker band 120. An alternative embodiment of the marker band 120 may comprise no perforations. The illustrated embodiment of the marker band 120 also comprises a generally cylindrical profile, though other profile shapes, e.g., oval, rectangular, square, etc., are within the scope of the invention. Additionally, for example, a marker band 120 comprising an incomplete cylinder and, therefore, wrapping incompletely around the metallic layer 106, may be provided.

Figure 6:
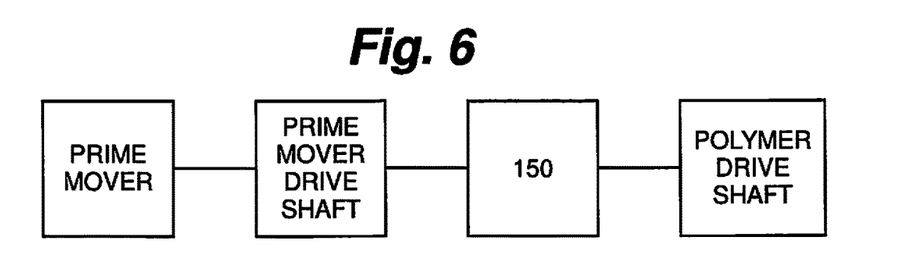
FIG. 6 is a schematic diagram illustrating the connection of elements for one embodiment of the present invention.
Figure 7:
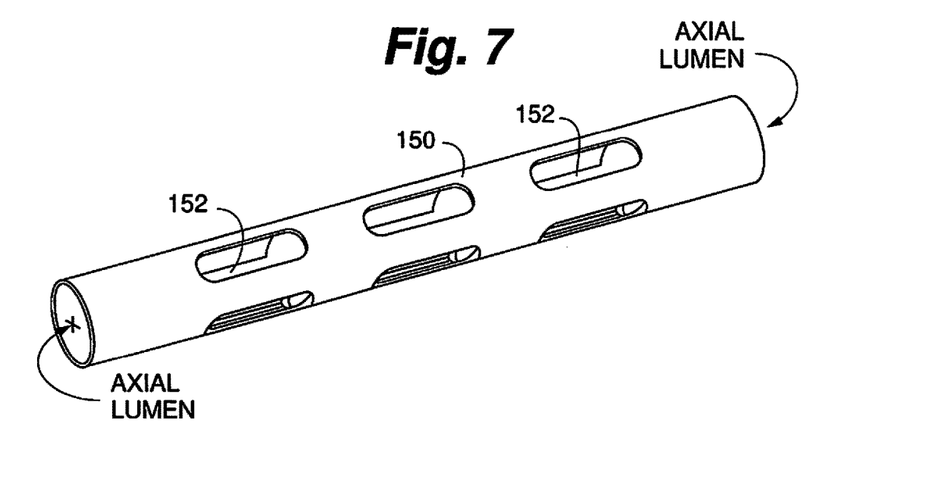
FIG. 7 is a perspective view of one embodiment of the present invention.
Figure 8:
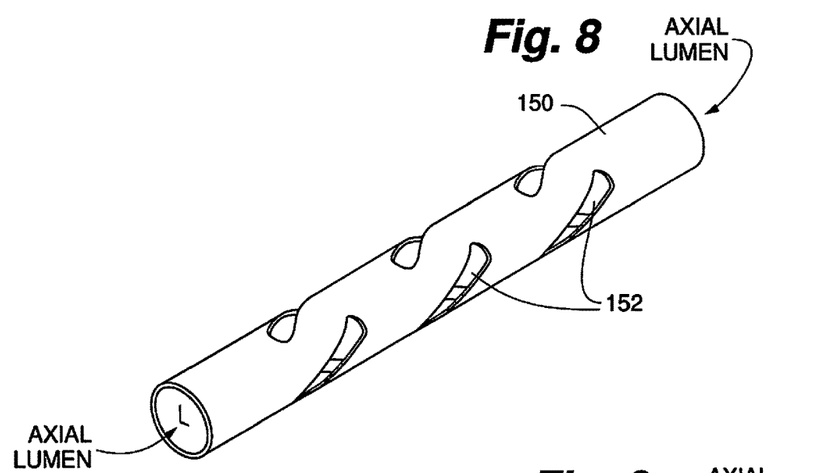
FIG. 8 is a perspective view of one embodiment of the present invention.
Figures 9, 10:
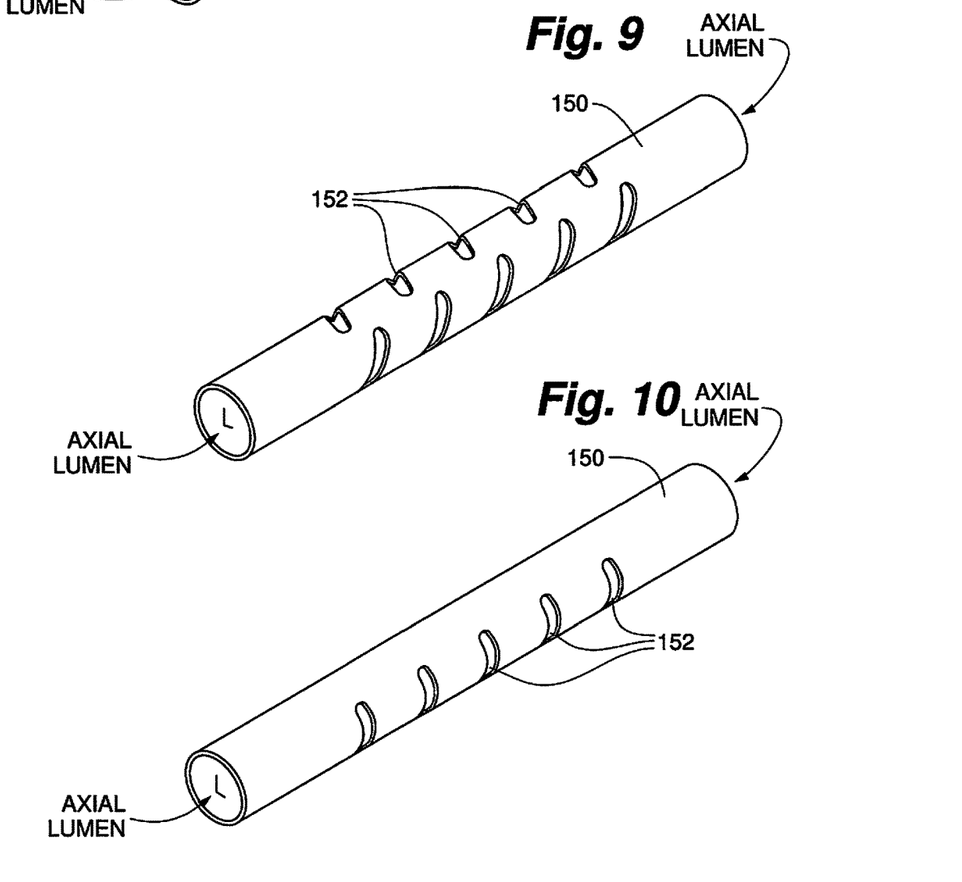
FIG. 9 is a perspective view of one embodiment of the present invention.
FIG. 10 is a perspective view of one embodiment of the present invention.

FIGS. 6-10 illustrate a coupler for the various embodiments of the polymer drive shaft described herein and for use with a system comprising the polymer driveshaft. The coupler 152 connects the prime mover, via a prime mover drive shaft, with the polymer drive shaft. This relationship is best seen in FIG. 6.

In the known systems, the coiled wire driveshaft 20 is formed with an uncoated multi-filar construction, providing gaps between the filars that allow or enable water and/or saline or other lubricating and/or cooling fluids to access the inner diameter of the coiled wire driveshaft 20.

Because the polymer driveshaft embodiments described herein are coated generally continuously on the outer and inner surfaces, there are no fluid access points along the driveshaft that will allow fluid to move into the inner diameter of the driveshaft.

Accordingly, the coupler 150 shown in various embodiments in FIGS. 7-10 is provided with openings 152 through the wall of the coupler 150 and comprising an axial lumen through the coupler 150. These openings may be located on the center line of the coupler or may be offset from the centerline. The openings 152 may be longitudinally shaped along the center line, or parallel with the centerline or axis of rotation. The openings 152 may alternatively be perpendicular to the center line or at some angle thereto, or some combination of any of these possible configurations as illustrated in the alternate embodiments of FIGS. 8-10. Further, there may be a single opening 152 or there may be more than one opening 152 in the coupler 150, configured to allow fluid to pass therethrough for subsequent access to the inner diameter of the polymer driveshaft embodiments disclosed herein.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible, and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A high-speed rotational medical system for use in conducting medical procedures within a patient's blood vessels, comprising:
    a handle comprising a rotational drive mechanism connected to a power source, the handle and power source located outside of the patient's body;
    a three-layered drive shaft in rotational engagement with the rotational drive mechanism, the three-layered drive shaft comprising a drive shaft lumen therethrough;
    a tool operationally attached to the three-layered drive shaft; and
    a guide wire advanceable within the drive shaft lumen, wherein the three-layered drive shaft is adapted to rotate over the guide wire,
    wherein the three-layered drive shaft further comprises three layers consisting of
        an outer polymer layer,
        an inner polymer layer, the inner polymer layer comprising a different polymer than the outer polymer layer and defining the drive shaft lumen therethrough and an inner surface that is generally smooth and continuous,
        a middle metallic layer disposed between the inner and outer polymer layers, and a metallic band affixed to the middle metallic layer, wherein the tool attached to the metallic band.

2. The high-speed rotational medical system of claim 1, further comprising the outer polymer layer comprising at least one of the group consisting of: nylon, polyether ether ketone (PEEK), and polyimide.

3. The high-speed rotational medical system of claim 1, further comprising the outer polymer layer comprising a composite formed from two or more of the group consisting of: nylon, polyether ether ketone (PEEK), and polyimide.

4. The high-speed rotational medical system of claim 1, further comprising the inner polymer layer formed of at least one of the group consisting of: polytetrafluoroethylene (PTFE), polyimide, nylon and polyether ether ketone (PEEK).

5. The high-speed rotational medical system of claim 1, further comprising the inner polymer layer comprising a composite formed from two or more of the group consisting of: polytetrafluoroethylene (PTFE), polyimide, nylon and polyether ether ketone (PEEK).

6. The high-speed rotational medical system of claim 1, wherein the tool operationally attached to the three-layered drive shaft is adapted for removing a lesion within a patient's blood vessel.

7. The high-speed rotational medical system of claim 6, wherein the tool operationally attached to the three-layered drive shaft further comprises an atherectomy tool selected from the group consisting of: an eccentric burr, a concentric burr, an eccentric abrasive crown, and a concentric abrasive crown.

8. The high-speed rotational medical system of claim 1, wherein the tool operationally attached to the three-layered drive shaft comprises one or more of the group consisting of: an atherectomy tool, one or more sensors, one or more transceivers, and one or more receivers.

9. The high-speed rotational medical system of claim 1, wherein the tool operationally attached to the three-layered drive shaft is adapted to obtain, send and/or receive data related to a patient's blood vessel.

10. The high-speed rotational medical system of claim 9, wherein the tool operationally attached to the three-layered drive shaft is adapted to obtain data related to the position and/or distance of the tool relative to a region of interest within the patient's blood vessel.

11. The high-speed rotational medical system of claim 9, wherein the tool operationally attached to the three-layered drive shaft is adapted to obtain data related to one or more of the group consisting of: the elastance of a region of interest within the patient's blood vessel, the compliance of a region of interest within the patient's blood vessel, the compliance of a region of interest within the patient's blood vessel, and the material composition of a region of interest within the patient's blood vessel.

12. The high-speed rotational medical system of claim 1, further comprising the three-layered drive shaft's outer polymer layer adapted to generate no fluid, tissue or particulate auguring during high-speed rotation.

13. The high-speed rotational medical system of claim 1, further comprising the three-layered drive shaft's inner polymer layer adapted to generate no fluid, tissue or particulate auguring within the drive shaft lumen during high-speed rotation.

14. The high-speed rotational medical system of claim 1, further comprising no fluid access points along or through the inner polymer layer or the outer polymer layer.

15. The high-speed rotational medical system of claim 1, wherein the drive shaft lumen is adapted to accommodate a guide wire comprising a 0.004 inch diameter and wherein the outer polymer layer, middle metallic layer and inner polymer layer comprise a wall, the wall comprising a thickness of between 0.003 and 0.006 inches.

16. A drive shaft for a rotational medical device, comprising:
 three layers, the three layers consisting of:
  an outer polymer layer,
  an inner polymer layer, the inner polymer layer comprising a different polymer than the outer polymer layer and defining a drive shaft lumen therethrough and an inner surface that is generally smooth and continuous, and
  a middle metallic layer disposed between the inner and outer polymer layers;
 a metallic band attached to the middle metallic layer of the drive shaft;
 and a tool operationally attached to the metallic band.

17. The drive shaft of claim 16, wherein the tool operationally attached to the metallic band further comprises an atherectomy tool selected from the group consisting of: an eccentric burr, a concentric burr, an eccentric abrasive crown, and a concentric abrasive crown.

18. The drive shaft of claim 16, wherein the tool operationally attached to the metallic band comprises one or more of the group consisting of: an atherectomy tool, one or more sensors, one or more transceivers, and one or more receivers.

19. The drive shaft of claim 16, wherein the tool operationally attached to the metallic band is adapted to obtain, send and/or receive data related to a patient's blood vessel.

20. The drive shaft of claim 19, wherein the tool operationally attached to the metallic band adapted to obtain data related to the position and/or distance of the tool relative to a region of interest within the patient's blood vessel.

21. The drive shaft of claim 19, wherein the tool operationally attached to the metallic band adapted to obtain data related to one or more of the group consisting of: the elastance of a region of interest within the patient's blood vessel, the compliance of a region of interest within the patient's blood vessel, the compliance of a region of interest within the patient's blood vessel, and the material composition of a region of interest within the patient's blood vessel.

* * * * *